United States Patent [19]
Crawford

[11] Patent Number: 6,086,904
[45] Date of Patent: Jul. 11, 2000

[54] ESSENTIAL OIL SOLID COMPOSITIONS

[75] Inventor: Ian Crawford, Sanctuary Cove, Australia

[73] Assignees: Teeteeoh Research Group Pty Ltd; P. Guinane Pty Ltd, both of New South Wales, Australia

[21] Appl. No.: 09/297,286

[22] PCT Filed: Oct. 24, 1997

[86] PCT No.: PCT/AU97/00716

§ 371 Date: Apr. 29, 1999

§ 102(e) Date: Apr. 29, 1999

[87] PCT Pub. No.: WO98/22152

PCT Pub. Date: May 28, 1998

[30] Foreign Application Priority Data

Nov. 20, 1996 [AU] Australia .................................. PO 3780
Apr. 1, 1997 [AU] Australia .................................. PO 5948

[51] Int. Cl.[7] .............................. A61L 9/015; A61L 9/04; A61L 35/78; A01N 65/00; A01N 25/00
[52] U.S. Cl. ...................... 424/405; 424/76.2; 424/76.3; 424/196.1; 424/409; 514/780; 514/782; 514/957
[58] Field of Search .................................. 514/783

[56] References Cited

U.S. PATENT DOCUMENTS

| 4,056,612 | 11/1977 | Lin | 424/76 |
| 4,374,814 | 2/1983 | Gaylord | 423/245 |
| 5,009,890 | 4/1991 | DiPippo | 424/195.1 |
| 5,382,410 | 1/1995 | Peltier | 422/121 |

FOREIGN PATENT DOCUMENTS

| 63-260956 | 10/1988 | Japan . |
| 1 241 914 | 8/1971 | United Kingdom . |
| WO 88/10122 | 12/1988 | WIPO . |

OTHER PUBLICATIONS

Derwent Abstract Acession No. 49152W/30, (Wassermann) Jul. 17, 1975.

*Primary Examiner*—S. Mark Clardy
*Assistant Examiner*—Konata M. George
*Attorney, Agent, or Firm*—Nixon & Vanderhye

[57] ABSTRACT

Solid composition including a gum material and an tea tree oil and optionally another essential oil wherein the solid composition releases vapor containing the essential oil when exposed to an effective flow of gas. A method of diffusing tea tree oil into the atmosphere and a method of disinfecting air conditioning systems are also provided.

37 Claims, No Drawings

ESSENTIAL OIL SOLID COMPOSITIONS

FIELD OF THE INVENTION

The present invention relates to solid compositions which release a vapour containing at least one essential oil when exposed to effective air flow. The present invention also relates to methods of producing the solid compositions; and to methods of disinfecting air conditioning systems using the solid compositions.

BACKGROUND OF THE INVENTION

Tea tree oil is a natural essential oil from a tree of the class Myrtenceae, especially of Melaleuca. Tea tree oil has been used as a broad spectrum topical antiseptic for more than 70 years. In recent times, the anecdotal evidence as to the antimicrobial efficacy of tea tree oils has been substantiated by scientific evidence. Such evidence can be found in the work of Carson, C. F. and Riley, T. V, *Antimicrobial activity of the Major Components of the essential oil of Melaleuca Alternifolia*, Journal Applied Bacteriology, 78, 264–269 (1995); C. F. Carson, B. D. Cookson, H. D. Farrelly and T. V Riley, *Susceptibility of methicillin-resistant Staphylococcus aureaus to the essential oil of Melaleuca Alternifolia*, Journal Antimicrobial Chemotherapy, 35, 421–424 (1995); and Carson, C. F., Hammer, K. A. and Reiley, T. V. (1996) *In vitro activity of the essential oil of Melaleuca Alternifolia against Streptococcus spp*. Journal of Antimicrobial Chemotherapy 37: 1177–1178.

It is well recognised that commercial, industrial and hospital air conditioning ducting can be a major source of infection and re-infection in public and private buildings. The World Health Organisation (WHO) reported its findings on this subject in 1988. This report in brief stated that biological air contaminants in indoor air have been associated with half of all absenteeism and reduced worker efficiency discovered in the report.

International publication No. WO 88/10122 (Commonwealth Industrial Gases Ltd) describes the use of a biocidal composition comprising an oil of Melaleuca in disinfecting air conditioning systems. This procedure involves solubilising the tea tree oil in both ethanol and carbon dioxide and delivering the solubilised tea tree oil by gaseous carbon dioxide into air conditioning ducting. The procedure therefore requires a constant supply of carbon dioxide by way of carbon dioxide gas cylinders. Specialised equipment such as a high pressure rated gun, hoses and other automatic delivery apparatus are also required. In addition to the fact that this procedure requires specialised equipment and highly trained personal, the possible hazards associated with the use of carbon dioxide in these procedures are well documented. A safer and more cost effective procedure for disinfecting air conditioning systems is therefore desirable.

The positive effects of dispersing pleasant aromatic essential oil odours into public building air space are now well described in the medical literature. The traditional manner for achieving this is by the use of either electric diffusers or by candle warmed water or oil dispersed essential oil burners.

At the Plane Tree Public Hospital in California patients are given a choice of fragrances. In the St Croix Valley Memorial Hospital, Wisconsin, natural fragrances are used to counteract unpleasant odours and to generally improve the atmosphere of all patient care and amenity rooms. The Sloane Kettering Institute in New York has reported that the use of Heliotropin, a vanilla like perfume, has significantly reduced stress in cancer patients. Lavender and Camomile essential oils are now in regular use in hospitals in the United Kingdom. Where elderly patients have demonstrated a tendency to insomnia the use of lavender has been found to lead to less restlessness and an actual increase in the number of hours sleep.

At the Japan School of Medicine the worker Sagano has reported that the use of natural fragrance will help both in the relaxation of staff and patients. International Airlines as Virgin Airlines and New Zealand Airlines are using pure essential oils to assist customers overcome travel fatigue and jet lag. International Hotel Groups as the Marriott Chain use essential oil odours in the lobby areas of many of their hotels.

In all of the examples cited above traditional methods of dispersing the natural essential oil odours are employed. It is desirable to develop a method of dispersing essential oils which eliminates the need for electrical or candle or other such diffusers.

SUMMARY OF THE INVENTION

The present inventors have now developed a solid composition which releases microscopic essential oil vapour when exposed to an effective flow of gas such as that generated by an air conditioning system. When placed in air conditioning ducts, solid compositions of the present invention release an essential oil vapour. In cases where the essential oil used in the solid composition exhibits antimicrobial activity, such as tea tree oil, the solid compositions release a germicidal oil vapour. These compositions therefore provide a relatively safe and inexpensive means for dispersing essential oils in a given environment or for disinfecting air conditioning systems.

Accordingly, in a first aspect the present invention provides a solid composition including a gum material and tea tree oil wherein the solid composition releases vapour containing the tea tree oil when exposed to an effective flow of gas.

The gum material may be any material classified as a gum or hydrocolloid including proteins, polysaccharides (for example, microbial polysaccharide exudates), carbohydrates and celluloses or mixtures thereof.

In a preferred embodiment, the gum material includes carrageenans extracted from red seaweeds. Rhodophyeae-Gigartinales, families Gigartinaceae and Solieriaceae and example species *Eucheuma coltinii, Chondrus crispus, Eucheuma spinosan* and *Gigarta stellata* are suitable red seaweeds for a source of primary gum materials.

In a further preferred embodiment the carrageenans include kappa, iota or lambda fractions or mixtures thereof.

In another preferred embodiment the gum material includes a galactomannan. Preferably, the galactomannan has a molecular weight of approximately 300.000 and is non-ionic. The galactomannan may be locust bean gum derived from the legume *Ceratonia siliqua*.

In another preferred embodiment the gum material includes a microbial exudate. The exudate may be derived from a bacterium such as *Xanthomonas campestris*. The microbial exudate may be Xanthan gum.

In a more preferred embodiment the gum material includes a mixture of two or more materials selected from carageenans, locust bean gum and Xanthan gum.

Preferably, the gum material is present in the solid composition at a concentration of between 2 and 10 wt %, more preferably between 3 and 6 wt %.

In a further preferred embodiment deionised water is used to prepare the gum material solution. Preferably, the pH of a 1% solution of the gum material solution is in the range of 7 to 9.

The term "essential oil" when used herein encompasses both synthetic essential oils and naturally occurring essential oils. Non-limiting examples of essential oils are oils of various fruits such as apple, cherry, pineapple and the like, oils of various woods such as cedar, pine, briar and the like, oils of various flowers or herbs such as ruses, violets, tobacco flowers and the like, and other such fragrances such as peppermint, menthol, camphor, methyl salicylate, eucalyptus, parachlor benzene, acetates and in general essential oils such as alcohols, aldehydes, esters, terpenes, tars, phenols, thaymols and the like.

In one preferred embodiment the essential oil exhibits antimicrobial activity. Non-limiting examples of oils which exhibit antimicrobial activity include oils obtained from tea trees, thyme, lemongrass, lemons, oranges, anise, clove, roses, lavendar, citronella, eucalyptus, pepermint, camphor, sandalwood and cedar and combinations thereof.

In a preferred embodiment the essential oil is an aromatic oil or a tea tree oil or a mixture thereof.

The aromatic oil may be selected from one or more of the group consisting of heliotropin, lavender, camomile, a lemon scented oil (such as the oil of *Leptospermum liversidgeii*), sandalwood and jasmine.

The essential oil of the species *Leptospermum liversidgeii* has a unique and long lasting natural lemon odour. The present inventors have found that compared to other lemon scented species (notably *Leptospermum petersoni*) this species delivers the most pleasant of lemon odours and does so for the longest duration.

In a further preferred embodiment, the solid composition also includes a fixative. By "fixative" we mean a component which prolongs the evaporation rate of an aromatic oil.

The fixative may be selected from the group consisting of musk ketone, coumarin, eugenol and vanillin. The natural hydrocarbon component eugenol is a preferred fixative for fragrant materials.

In the oil of *Leptospermum liversidgei*, eugenol is present in relatively high amounts. This factor combined with the other constituents such as citronellal, alpha pinene, linalool and thymol work together to produce naturally a long lasting pleasant lemon aroma. The present inventors have found that by combining the natural fixative elements present in the oil of *Leptospermum liversidei*, unique and pleasant long lasting aromatic blends containing lavender or camomile can be produced. The finished aroma can have a lemon scent or it can display the fragrance of lavender or camomile. These examples are non-limiting and any combination of fragrances that can be incorporated into solid gum compositions are encompassed by the present invention.

Preferably, the essential oil is present in the solid composition at a concentration of between 5 and 20% v/v, more preferably between 10 and 15% v/v.

The essential oil may be solubilised by any known means such as by admixture with an alcohol or a surfactant or a mixture thereof. The alcohol may be ethanol, propan-2-ol (isopropyl alcohol), propylene glycol or methanol.

In a preferred embodiment, the essential oil is solubilised by admixture with a non-ionic surfactant which allows a low weight surfactant to weight of tea tree oil composition. Preferably, the surfactant is an alcohol ethoxylate. In a more preferred embodiment, the alcohol ethoxylate is polyoxyethylene (2) oleyl ether.

In a second aspect the present invention provides a method of solubilising an essential oil which includes
 i) heating a predetermined amount of an alcohol ethoxylate to a temperature of between 25° C.–45° C.; and
 ii) adding a predetermined amount of the essential oil to the heated alcohol ethoxylate.

The preferred method of solubilising essential oil provided by the present invention is advantageous in that it results in an essential oil solution wherein the weight to weight ratio of surfactant to tea tree oil is relatively low. Weight to weight ratios of less than 1 to 1 can be achieved by following the solubilisation method of the present invention.

The low weight to weight surfactant to essential oil solutions are preferable for the following reasons:
 i) High weight to weight surfactant to essential oil mixtures often give rise to solutions which are hazy, cloudy or opalescent. These cloudy or opalescent solutions are generally not desirable for commercial reasons. The low weight to weight surfactant to essential oil solutions can be diluted with water to produce bright clear solutions.
 ii) A relatively high mass of surfactant can inhibit the broad spectrum germicidal efficacy of an essential oil such as tea tree oil. The lower the weight surfactant the higher the efficacy of natural oil as measured by standard Minimum Inhibitory Concentration (MICS) analysis.

In a further preferred embodiment of the present invention, the solid composition is in the shape of a disc.

In a further preferred embodiment the disc is a flat discus shape with a base surface and a top surface and a side wall connecting the base surface to the top surface. Preferably, the diameter of the top surface is less than the diameter of the base surface.

In a preferred embodiment the ratio of the height of the side wall to the width (circumference) of the top surface is between 1:10 and 1:11.5. For example, a preferred disc may have a side wall height of 20 mm and a top surface width (circumference) of 230 mm. A disc of the present invention may, for example, have the following dimensions:
 Base surface: 250 mm
 Top surface: 210 mm
 Height: 40 mm.

In a further preferred embodiment the side wall is shaped in a camber. Preferably, the angle of connection between the base and top surfaces is equal to or less than 65 degrees and more preferably equal to or less than 62 degrees and 57 minutes.

In a further preferred embodiment the solid compositions of the present invention have a total weight of between 0.5 and 5 kg. More preferably, the solid compositions have a total weight of between 0.9 and 3 kg.

The preferred dimensions of a disc according to the present invention provide an advantage in that a slow and even diffusion of natural oil from the disc occurs in the presence of air flow.

In a third aspect the present invention provides a method of preparing a solid composition which method includes
 i) dissolving a gum material in an aqueous solution:
 ii) heating the gum material solution to a temperature of between 60° C. and 95° C.;
 iii) admixing the heated gum material solution with a tea tree oil/surfactant solution; and
 iv) placing the admixed solution from step iii) into a mould.

It will be appreciated that the present invention provides a simple and cost-effective means for dispersing essential oils in a given environment. The solid compositions of the present invention can be simply placed in air conditioning ducts by unskilled labour so as to diffuse essential oils into the air stream.

Accordingly, in a fourth aspect the present invention provides a method of diffusing tea tree oil into the atmosphere which method includes exposing a solid composition including a gum material and the tea tree oil to an air flow such that the solid composition releases vapour containing the tea tree oil.

In a preferred embodiment the solid composition is exposed to an air flow by placing the solid composition in an air conditioning duct.

It will be appreciated that the preferred solid compositions of the present invention also provide a simple and cost effective means of disinfecting air conditioning systems. Unlike systems described in the prior art, the preferred compositions of the present invention do not rely on solubilising the essential oil in alcohol or gaseous carbon dioxide. The preferred non toxic water-based gum disc-shaped compositions allow germicidal oil vapour to diffuse slowly and constantly in the presence of the air flow generated in air conditioning ducting.

Accordingly, in a fourth aspect the present invention provides a method of disinfecting an air conditioning system which method includes placing a solid composition in a duct of the air conditioning system, the solid composition including a gum material and tea tree oil, wherein the composition releases antimicrobial vapour containing the tea tree oil when exposed to an effective flow of gas.

In a preferred embodiment, the essential oil is tea tree oil.

The term "air conditioning system" as used herein refers collectively to ducts, fans, filters, humidifiers, coolers and other plant and equipment assembled for air conditioning to parts of such systems.

DETAILED DESCRIPTION OF THE INVENTION

In order that the nature of the present invention may be more clearly understood preferred forms thereof fill now be described with reference to the following Examples.

EXAMPLE 1

Tea Tree Oil Compositions

In a preferred embodiment of the invention the tea tree oil is manufactured in accordance with the ISO 4730 standard. Preferably, the tea tree oil is a pharmaceutical grade material. Table 1 describes the characteristics of an ISO 4730 standard tea tree oil. In a most preferred embodiment the tea tree oil conforms with the ISO 4730 standard prescribed in Table 1 but with component values in respect to 1,8 cineol less than 4% and preferably 2.2–3.0%; and terpinen-4-ol values greater than 37% and preferably 39–41%. Table 2 shows results of gas chromatic analysis for two batches of the preferred TEETEEOH! brand pharmaceutical grade tea tree oil.

TABLE 1

The ISO Standard 4730 prescribes the following physical and component details for Australian Single Distilled Tea Tree Oil -Oil of Melaleuca Alternifolia

| | |
|---|---|
| Physical State | Liquid |
| Colour | Visually colourless to pale yellow |
| Odour | Typically Myristic |
| Specific Gravity | Method ISO 279 20 Degrees C/20 degrees C 0.885–0.906 |
| Refractive Index | Method ISO 280 1.475 to 1.482 |
| Optical Rotation | Method ISO 592 +5 degrees to +15 degrees |
| Solubility | In 85% V/V Ethanol at 20 Degrees C the Miscibility should be such that one volume of the oil shall require not more than two volumes of 85% ethanol to give a clear solution This is tested in accordance with ISO Method 875 |
| Flash Point | Penskey Martens Closed Cup IP 34 In typical Range 57 degrees C to 60 Degrees C |
| Fire Point | Cleveland Open Cup IP 36–72 Degrees C. |
| Component Range | There are 15 components determined by gas chromatographic analysis in accordance with method ISO 7609-1985 which are identified as being truly representative of genuine oil of melaleuca alternifolia in the TSO 4730 standard. These are listed below. The components described as Ledene (Viridiflorene), delta-Cadinene, Globulol and Viridiflorol are each components found only in the prescribed rations in genuine oil of melaleuca alternifolia and are said to be "genuine marker components for tea tree oil (oil of melaleuca alternifolia)." |
| Component | ISO 4730 Range % |
| alpha-Pinene | 1–6 |
| Sabinene | Trace–3.5 |
| alpha-Terpinene | 5–13 |
| Limonene | 0.5–4 |
| para-Cymene | 0.5–12 |
| 1,8 Cineole | 0–15 |
| gamma-Terpinene | 10–28 |
| Terpinolene | 1.5–5 |
| Terpene-4-ol | 30 plus |
| alpha-Terpineol | 1.5–8 |
| Aromadendrene | Trace–7 |

TABLE 1-continued

The ISO Standard 4730 prescribes the following physical and component details for Australian Single Distilled Tea Tree Oil -Oil of Melaleuca Alternifolia

| Physical State | Liquid |
|---|---|
| Ledene (Viridiflorene) | 0.5–6.5 |
| delta-Cadiuene | Trace–8 |
| Globulol | Trace–3 |
| Viridiflorol | Trace–1.5 |

TABLE 2

Teeteeohl Brand Pharmaceutical Single Distilled Australian Tea Tree Oil (Oil of Melaleuca Alternifolia)

| COMPONENT | VALUE % | ISO 4730 STANDARD % |
|---|---|---|
| Batch Number 1029 | | |
| alpha-Pinene | 0.7 | 1–6 |
| Sabinene | 0.5 | Trace–3.5 |
| alpha-Terpinene | 9.7 | 5–13 |
| Limonene | 1.0 | 0.5–4 |
| para-Cymene | 2.7 | 0.5–12 |
| 1,8 Cineole | 2.8 | 0–15 |
| gamma-Terpinene | 20.9 | 10–28 |
| Terpinolene | 3.4 | 1.5–5 |
| Terpinen-4-ol | 40.0 | 30 plus |
| alpha-Terpineol | 2.5 | 1.5–8 |
| Aromadenedrene | 1.3 | Trace–7 |
| Lendene (Viridiflorene) | 1.1 | 0.5–6.5 |
| delta-cadinene | 1.1 | Trace–8 |
| Globulol | 0.4 | Trace–3 |
| Viridiflorol | 0.2 | Trace–1.5 |
| BATCH 1021 | | |
| alpha-Pinene | 2.4 | 1–6 |
| Sabinene | 0.6 | Trace–3.5 |
| alpha-Terpinene | 10.1 | 5–13 |
| Limonene | 1.0 | 0.5–4 |
| para-Cymene | 2.3 | 0.5–12 |
| 1,8 Cineole | 3.0 | 0–15 |
| gamma-Terpinene | 20.8 | 10–28 |
| Terpinolene | 3.4 | 1.5–5 |
| Terpinen-4-ol | 41.4 | 30 plus |
| alpha-Terpineol | 2.6 | 1.5–8 |
| Aromadenedrene | 1.1 | Trace–7 |
| Lendene (Viridiflorene) | 0.9 | 0.5–6.5 |
| delta-cadinene | 0.9 | Trace–8 |
| Globulol | 0.3 | Trace–3 |
| Viridiflorol | 0.2 | Trace–1.5 |

EXAMPLE 2
Tea tree oil solid composition

A carrageenan locust bean gum mixture is selected which has been standardised with the addition of appropriate salts and polysaccharides so the mixture possesses the following characteristics: Viscosity: 400 to 600 centipoises measured as a 2.5% aqueous solution on a Brook field RVT Viscometer, operating at 20 revolutions per minute and with solution heated to 70 degrees centigrade.

The pH of the Carrageenan, locust bean gum mixture is in the range 7–9% when a 1% solution of the mixture is measured.

The particle size of the combined dried mixture is such that more than 98% is finer than 250 microns. The total moisture content of the mixture is not greater than 14%. The gel strength of the mixture is between 1800 and 2200 measured in a Kobe tester a solution strength of 2.5%. The carrageenans are a mixture of kappa and iota component containing types.

The water for first dispersing the carrageenan and locust bean gum mixture and then heating to gelatinisation is de-ionised water.

The carrageenan locust bean gum mixture is first wetted to aid dispersion with ethanol. A mixture of pure tea tree oil and surfactant is made. The tea tree oil is as described above and conforms with ISO 4730. The actual tea tree oil used is TEETEEOH! Brand Australian Single Distilled Pharmaceutical Grade with the following important component values; the 1, 8 cineole is in the range 2.2–2.5% and the Terpinene-4-ol in the range 39–41%.

The surfactant used is polyoxyethylene (2) oleyl ether. The surfactant is measured so that sufficient is available to solubilise the tea tree oil. The measured surfactant is heated approximately 37 degree C. The carefully measured tea tree oil is poured into the heated surfactant and stilled vigorously. The finished solution is bright and clear. Sufficient de-ionised water is added to the surfactant-tea tree oil mixture as is required. This bright clear mixture is set aside.

The wetted carrageenan-locust bean gum mixture described above is mixed with sufficient cold water. The water temperature is no greater than 12 degrees C. The well dispersed carrageenan-locust bean gum mixture is gradually heated with vigorous stirring to 90 degrees C. The mixture is held at 90 degrees C. for several minutes. The mixture is allowed to cool to 70 Degrees C. To the cooled carrageenan-locust bean gum mixture is added the tea tree oil-surfactant solution. This has the immediate effect of rapidly cooling the mixed solution further. The cool mixture is poured carefully into rubber moulds. The moulds are formed so that the finished gel has a distinctive flat discus shape as described previously. The surface area of the top of the discus shape is preferably less than the surface area of the bottom of the discus shape. The ratio of the height (side wall) of the discus to its surface is preferably of the order of 1:10 or 1:11.5 but this ratio is not essential. The edge of the discus shape is preferably carefully shaped so as to provide a gradual camber. This is preferable so that even air diffusion takes place with the finished Tea Tree Gel Disc. The mixture can be de-moulded with 30 minutes. The Tea Tree Gel-Discs so formed are allowed to cool completely.

Upon complete cooling the discs may be packed in suitable plastic and further packed in recyclable cardboard cartons. The plastic may be polyethylene-plastics does type 4, polypropylene-plastics code type 5, or preferably Fluorinated—High density Polyethylene-plastics code type 2-modified. No colouring matter is used in the manufacture of any type of Tea Tree Gel-Disc. The final Tea Tree Gel Disc in this example contains 10% tea tree oil. The Tea Tree Gel Disc in this example has a shelf life of 12 months wrapped and packaged. The tea Tree Gel Disc in this example has an unwrapped normal room air circulation life of between 30 and 45 days.

When installed into an air conditioning ducting this Tea Tree Gel Disc may have a life of between 7 and 10 days. The Gel Disc life in an air conditioning system is dependent on the systems air flow and air temperature. The tea tree gel disc manufactured in accordance with this method can be described as having low to very low syneresis.

EXAMPLE 3

Tea tree oil solid composition

A carrageenan locust bean and xanthan gum mixture is selected which has been standardised with the correct addition of salts and saccharides. The carrageenan has a viscosity of 400 to 600 centipoises as measured in a 2.5% solution on a Brookfield RVT viscometer at 20 revolutions per minute and solution heated to 70 degrees C. The pH of the carrageenan in a 1% solution is between 7 and 9. The total moisture of the powder is 14%. The carrageenan tests to a gel strength of 1800 to 2200 in a Kobe test measured at 2.5% in de-ionised water. The carrageenan selected is a mixture of carrageenans containing kappa and iota component carrageenans. This mixture is dry mixed with a selected xanthan gum. The dry blended mixture is carefully weighed. To this weighed mixture is added sufficient ethanol to aid dispersion in cold de-ionised water. The mixture is slowly dispersed in di-ionised water with a commencement temperature of 12 degrees C. The water is added so that the final gel mixture contains 3.8% selected hydrocolloids. The mixture is gradually heated to 90 degrees C. under constant stirring. The heated mixture is held at 90 degrees C. under constant stirring for several minutes. To this mixture is added pre-prepared tea tree oil—surfactant solution of sufficient strength so that the final gel-disc contains no less than 10% v/v tea tree oil. The Tea Tree Oil in Pharmaceutical Standard Material conforming with ISO 4730.

The tea tree oil surfactant mixture is added to the hydrocolloid solution which has been cooled to 70 degrees C. The mixture is carefully stirred and allowed to cool further. It is then poured carefully into rubber moulds designed in accordance with disc specifications previously described. The moulds are released within 30 minutes. The gel discs are allowed to cool. Once cooled the Tea Tree Gel Discs may be packed in suitable plastic film and packed in recyclable fibreboard.

The Tea Tree Gel Discs manufactured in accordance with the method may have an air conditioning air diffusion life of between 7 and 10 days. The Gel Discs so produced are bright, shiny and almost transparent. No colouring material is used. The tea tree gel disc is manufactured in this manner can be described as having low syneresis.

EXAMPLE 4

Tea tree oil solid composition

In this example only pure kappa component type carrageenan from the family Solieriaceae species *Eucheuma cottonii* is used. Further, the ethanol alcohol which is used to aid dispersion of the carrageenan is also co-used to solubilise the pharmaceutical grade tea tree oil. No surfactants are used in this example. To the carrageenan as selected is added dextrose monohydrate and maltodexterin with a dextrose equivalent of between 17 and 21. The dry powder is carefully wetted with a proportion of the ethanol and mixed. To this wetted mixture is added cold water with a temperature of 12 degree C. The mixture is heated to 85 degrees C. and held for exactly 2 minutes. This solution is cooled to 70 degrees C. To the cooled mixture is added a pre mixed solution of ethanol and pharmaceutical grade tea tree oil. The tea tree oil conforms with ISO 4730 standard. The mixture is stirred vigorously. The rapidly cooling mixture is poured into suitable rubber mould prepared in accordance with the disc specification described previously. Within 15 minutes the moulds are released and the Tea Tree Gel Discs removed. The Tea Tree Gel Discs are allowed to cool completely. They may be packed in suitable plastic film as described previously. The plastic wrapped tea tree gel discs may be packaged in recyclable fibreboard boxes. The tea tree gel discs manufactured in this manner are preferably bright and clear and have reasonably hard finished surface. The tea tree gel disc made in the manner in this example have a tea tree oil content of 15%. The solid hydrocolloid matter is 4.8% and the weight of the finished tea tree gel discs is 900 grams. The air diffusion life in standard air conditioning ducting for this example was between 7 and 10 days. These discs can be described as having low to very low syneresis.

EXAMPLE 5

Tea tree oil solid composition

Pure kappa component carrageenan derived from *Eucheuma cottonnii* was used in this example. No additional salts or saccharides were used. The weighted carrageenan was wetted only with commercial methylated spirits. The wetted kappa carrageenan was thoroughly mixed and admixed with cold water at 20 degrees C. The mixture was well dispersed. A pre-prepared mixture of pharmaceutical grade tea tree oil and ethanol was then added to the cold kappa carrageenan mixture. The proportion of ethanol to tea tree oil in the pre-prepared mixture was approximately 2 parts ethanol to 1 part tea tree oil. The complete mixture was stirred vigorously and heated slowly to 85 degrees C. The mixture was kept at 85 degrees C. for approximatley 45 seconds. By way of a jacketed mixer cold water with temperature of between 12 and 14 degrees C. was introduced into the jacket as a cooling medium. The mixture was rapidly cooled to below 70 degrees C. and poured directly into suitable moulds as previously described. The moulds were released in 12 minutes. The tea tree gel discs allowed to cool. The Tea Tree gel discs made in this manner contained 15% tea tree oil v/v and were carried by a total dry hydrocolloid matter of 5%. The tea tree gel disc were packed as previously described. These discs were found to have an air conditioning diffusion life of between 7 and 10 days. They can be described as low syneresis.

EXAMPLE 6

Tea tree oil solid composition

A dry mixture of selected kappa and iota component carrageenans together with locust bean gum, xanthan gum, dextrose monohydrate, 17 DE maltodextrin, and cations including Sodium salts, Potassium salts and Calcium salts is carefully prepared. The weight of this mixture is such that the weight of mixed hydrocolloid in the final preparation is 3%. This mixture is wetted with ethanol. The mixture is carefully dispersed in cold water of a temperature between 8 and 12 degrees C. The mixture is mixed in a jacketed vessel with accurately controlled heating and cooling capabilities. The stirred mixture is carefully heated to 86 degrees C. and held at this temperature for 2 minutes. To this mixture is added a surfactant solubilised pharmaceutical grade tea tree oil mixture. The tea tree oil mixture is such that in the finished gel disc the tea tree oil content will be 10% v/v. The tea tree oil surfactant mixture is added when the hydrocolloid solution is at 65 degrees C. The total mixture is stirred carefully so as to minimise formation of air bubbles. The cooling mixture is carefully poured into the rubber moulds as previously described. Within 30 minutes the mould can be released. The Tea Tree Gel Discs are left to cool for 24 hours prior to packing. The gel discs made in this manner have very low syneresis. After 24 hours the tea tree gel discs are packed in selected plastic film. The plastic film wrapped tea tree gel discs are placed into recyclable fibreboard for storage and shipping. No colouring matter is used and the tea tree gel discs have a pleasant opaque creamy to light brown colour. The Tea Tree Gel Discs made in this way have very low syneresis. The rate of diffusion in standard air conditioning systems may be 7 to 10 days depending on air flow and temperature range. The net weight of tea tree gel disc made in this manner is 900 grams each. The total volume of tea tree oil dissipated in 168 hours is approximately 90 grams. In the first 24 hours 18 grams of tea tree oil is dissipated. This is an approximate equivalent of 0.75 grams per hour in a typical air flow situation. This is relatively low yet as per the experimental results described herein is highly effective in the disinfecting of air conditioning ducting.

EXAMPLE 7
Tea tree oil and lavender solid composition

A carrageenan locust bean gum mixture is selected which has been standardised with the addition of appropriate salts and polysaccharides so the mixture possesses the following characteristics;

Viscosity; 400 to 600 centipoises measured as a 2.5% aqueous solution on a Brookfield RVT Viscometer, operating at 20 revolutions per minute and with solution heated to 70 degrees centigrade.

The pH of the Carrageenan locust bean gum mixture is in the range of 7–9 when a 1% solution of the mixture is measured.

The particle size of the combined dried mixture is preferably such that more than 98% is finer than 250 microns, the total moisture content of the mixture is preferably less than 14%. The gel strength of the mixture is between 1800 and 2200 measured in a Kobe tester at solution strength of 2.5%. The carrageenans are a mixture of kappa and iota component containing types.

The carrageenan locust bean gum mixture is first wetted to aid dispersion with ethanol. A mixture of pure tea tree oil, oil of *Leptospermum Liversidgeii*, oil of *Lavendula angustifolia* (lavender) and surfactant is made. The tea tree oil is as already described and conforms with ISO 4730. The additional oils are pure as defined by the Australian Standards.

The surfactant used is polyoxyethylene (20) oleyl ether. The surfactant is measured so that sufficient is available to solubilise all the essential oils described.

The measured surfactant is heated to 37 degrees C. The measured essential oils are poured into the heated surfactant and stirred vigorously. The finished solution is preferably bright and clear. Sufficient water is added to the surfactant—essential oil mixture as required. This bright highly fragrant mixture is set aside.

The wetted carrageenan—locust bean gum mixture described above is mixed with sufficient cold water. The water temperature is no greater than 12 degrees C. The well dispersed carrageenan-locust bean gum mixture is gradually heated with vigorous stirring to 90 degrees C. and held at this temperature for several minutes. The mixture is allowed to cool to 70 degrees C. To the cooled carrageenan-locust bean gum mixture is added the essential oil—surfactant solution. This has the immediate effect of rapidly cooling the mixed solution further.

The cooled mixture is poured into suitable moulds. The cooled discs are packed in such a way as to have a shelf life of 12 months wrapped. Unwrapped discs have been found to have an operational air conditioning ducting lift up to 30 days.

When installed into an air conditioning ducting the discs release a pleasant lavender fragrance.

EXAMPLE 8
Fragrant tea tree oil solid composition

In this example, custom made and chosen fragrant essential oil blends are selected, so that when incorporated with polysaccharides as previously described, the fragrance will diffuse into air conditioning ducting. Firstly, the fragrant essential oils are selected and blended so that the chosen fragrance is the most powerful of all fragrances present in the mixture. This blend of essential oils is then solubilised in a selected volume of polyoxyethylene (20) oleyl ether. This mixture is then added to a pre-prepared complex polysaccharide mixture which may comprise both kappa and iota type carrageenans and locust bean gum and guar gum.

In this example the most dominant fragrance is that of German Camomile essential oil derived from the species *Matricaria recutica*.

The method of preparation is similar to other examples described herein.

EXAMPLE 9
Tea tree oil and sandalwood solid composition

In this example and by way of demonstration that a single essential oil fragrant note could be achieved, by combining only one other essential oil with the oil of *Melaleuca alternifolia* (tea tree oil) as previously described. In this example only the oil of *Santalum album* (sandalwood) was added to that of the tea tree oil.

Whilst maintaining the broad spectrum antimicrobial characteristics of tea tree oil this example shows that the highly aromatic and myrsitic odour of tea tree oil can be simply masked and overpowered by an essential oil such as sandalwood. This is surprising given that sandalwood is described generally in essential oil and perfumery literature as the base note essential oil having an evaporation rate of 100 according to the index ascribed to Poucher. This index asserts that an oil with a maximum score of 100 has the slowest evaporation rate. By way of comparison, an oil such as lavender which is given an index number of 4, is considered to be a top note essential oil.

The sandalwood tea tree oil mixture is combined with a sufficient amount of polyoxyethylene (20) oleyl ether for solubilisation and the mixture added to a cooled mixture of complex polysaccharides. The combined mix is then poured into a suitable mould to form a disc shape as previously described.

The unwrapped discs so produced can deliver a pleasant fragrance when installed into air conditioning ducting. In circumstances where the air conditioning fans are operating (not necessarily the refrigeration) the sandalwood—tea tree oil solid composition discs may last for up to 30 day.

EXAMPLE 10
Summary of test results from trials conducted in air conditioning systems in a hospital in New South Wales, Australia The experimental parameters for establishing the broad spectrum germicidal efficacy of the air diffused water gel tea tree oil solid compositions is described below;

An air conditioning ducting system was chosen in a major New South Wales Australia Public Hospital.

This system operated on refrigerated air and the the refrigerant was of a non CFC type. The air flow was variable to suit and was measured typically as cubic metres per minute.

The temperature range of the air flow was measured and automatically controlled so that at ducting inspection points the air temperature ranged between 11 degrees C. and 21 degrees C.

Specially adapted ease of access inspection ports were installed at the selected air conditioning ducting.

Ducting with identical geometry was selected in two separate floors-nominated as level 3 and level 4.

Only active air diffused water gel blocks containing water miscible tea tree oil weer installed on level 3. On level 4 either no gel discs or only placebo gel discs were installed for control purposes.

Installation was in the manner that two tea tree oil solid compositions were installed within 600 mm either side of the inspection ducting, so that one solid composition was up airstream and one down airstream from the inspection port.

The solid compositions were placed on the flat floor of each ducting either side of the inspection port as described above.

The width of the ducting floor was at point 1 level 3 approx 600 mm. The width of the ducting floor at point 2 level 3 was approximately 350 mm.

The ducting floor widths at identical inspection points on level 4 were approximately the same as those on level 3.

The air flow into the ducting selected had an airstream which has been HEPA micro filtered (High Efficiency Particulate Air Filtered).

The ducting systems on both level 3 and level 4 were carefully sampled for both air and surface microbiological samples as per the accompanying table/s.

The sampling was carried out by independent Air Quality Surveyor using the most modern air and surface sampling methods and equipment.

The sampling was further supervised by a qualified and practising microbiologist.

The solid compositions were produced by the method described in example 2 and were installed on level 3 at 1 inspection point approximately 1 hour after this initial sampling.

Further sampling was performed on the same active sites described as inspection points 1 and 2 on level 3 approximately 21 hours later.

Approximately 72 hours after the insertion of the first two solid compositions, which were only installed at inspection point 1, an additional four solid compositions were installed on level 3.

Two solid compositions were installed at inspection point 1 on either side of the inspection port. Two solid compositions were installed at inspection point 2 level 3 on either side of the inspection port-in floor of the ducting.

The distance between inspection point 1 and 2 is approximately 20 metres.

First Microbiological samplings were taken prior to installation of the first two solid compositions; further samplings were taken after the installation of the additional four solid compositions; installed as two at each inspection point.

The results obtained from these samplings show clearly the microbiological efficacy of the solid compositions.

The reduction in Fungal count within the first 21–24 hours was particularly significant as fungal contamination of air conditioning ducting is of major concern to health and sanitation authorities. The results show a greater than 100 fold reduction after 48 hours. In fact in the first 21 hour period the fungal reduction was greater than 800 fold being reduced from greater than 3200 colony forming units (CFU) to less than 4 CFU.

The rate of diffusion of the solid compositions was as predicted by small scale experimental programmes and indicated as 20% within the first 24 hours, 20% in second 24 hours, approximately 20% in the third 24 hour period. Thereafter the rate of diffusion was at around 10% in each 24 hour period and reducing so that the total solid composition had air diffused within the air conditioning ducting by the action of the air flow existing within the system in a period of between 120–168 hours.

The results obtained from the trials above are further confirmation of the well published efficacy data for tea tree oil which shows the Minimum Inhibitory Concentrations of Australian Tea Tree oil for some organism as per the table below:

|  | MIC % |
|---|---|
| GRAM POSITIVE BACTERIA | |
| Bacillus cereus | 0.3 |
| Bacillus subtilus | 0.3–0.4 |
| Corynebacterium spp | 0.2–0.3 |
| Micrococcus luteus | 0.2–0.3 |
| Propionibacterium acnes | 04–0.5 |
| Methicillin resistant Staphylococcus aureus | 0.2–0.3 |
| Staphylococcus epidermis | 0.5 |
| Enterococcus faecalis | 0.5–0.75 |
| GRAM NEGATIVE BACTERIA | |
| Enterobacter aerogenes | 0.3 |
| Eschericia coli | 0.2 |
| Klebsiella pneumoma | 0.3 |
| Proteus vulgaris | 0.2–0.3 |
| Pseudomonas putida | 0.5 |
| Serratia marcescens | 0.2–0.3 |
| FUNGI AND YEASTS | |
| Aspergillus niger | 0.3–0.4 |
| Aspergillus flavus | 0.4–0.5 |
| Candida albicans | 0.2 |
| Piryrosporum ovales | 0.2 |
| Trychophyton mentagrophytes | 0.3–0.4 |
| Trychophyton nibrum | 1.0 |

EXAMPLE 11

Summary of test results from trials conducted in air conditioning system in a public hospital in New South Wales, Australia Sampling performed by Air Quality Services Pty Ltd and Microbiological examination of the samples performed by Biotech Laboratories Pty Ltd Queensland.

Test Area

Air conditioning air ducting system. The system comprises straight ducting with two in—place inspection points at approximately 25 metres apart.

Air Supply

The system is refrigerated and works on constant supply 24 hours 7 days per week. The air is HEPA filtered.

Microbiological Sampling

Sampling for airborne bacteria, airborne fungi and mould, surface bacteria and surface yeast and mould was performed by sterile swab and automatic air sampling apparatus.

Solid Composition Tea Tree Oil Gel Discs

Solid compositions for this test were produced according to the method described in Example 2. Two each with a total mass of 2.2 kilograms were placed at each inspection point. The water solubilised tea tree oil content in each gel disc was 12% v/v.

Sampling Procedure

Samples were taken prior to installing the gel discs. The gel discs were installed either side of the inspection hatch and placed directly on the floor of the air conditioning ducting.

Bacteria

Both surface and airborne bacteria levels tested were shown to be so insignificant as unnecessary to be reported in these results.

Surface Yeast and Mould and Airborne Fungi and Mould

These tests indicated very high microbiological contamination.

RESULTS

|  | Date | | | |
|---|---|---|---|---|
|  | 05/11/96 | 06/11/96 | 13/11/96 | 19/11/96 |
|  | SURFACE YEAST AND MOULD CFU/cm | | | |
| LEVEL 3 |  | 24 Hour Result |  | Final Result |
| ACCESS POINT 1 | Temp/C 12 | Temp/C 20 | Temp/C 15 | Temp/C 13 |
| Against Flow | 44 | 36 | 160 | 20 |
| With Flow | 8 | 120 | 100 | 8 |
| Hatch | >1200 | 4 | <4 | <4 |
| Hatch | 8 | <4 | <4 | <4 |
| ACCESS POINT 2 | | | | |
| Against Flow | >1200 | <4 | 12 | 8 |
| With Flow | 16 | 8 | 8 | 4 |
| Hatch | <4 | <4 | <4 | <4 |
| Hatch | <4 | 16 | <4 | <4 |

AIRBORNE FUNGI AND MOULD CFU/cm

| ACCESS POINT 1 | | | | |
|---|---|---|---|---|
| Against Flow | 150 | 50 | <50 | <50 |
| With Flow | 100 | 150 | <50 | 100 |
| ACCESS POINT 2 | | | | |
| Against Flow | 150 | 50 | <50 | <50 |
| With Flow | <50 | 200 | 50 | >50 |

The tea tree oil solid compositions were installed on Nov. 5, 1996 (after initial samples taken). These results show significant surface yeast and mould at the start of the trial. The 24 hour reduction (as measured on Nov. 6, 1996) of the greater than 1200 CFU values indicate the efficacy of the solid tea tree oil gel discs. The final 14 day results further indicate this efficacy.

Airborne Fungi and Mould can be described as insignificant levels. A statistical reduction is observed.

EXAMPLE 12

Test conditions and results obtained from trials conducted in a major public Bowling Club in Northern New South Wales—Australia.

Sampling performed by Air Quality Services Pty Ltd and Microbiological examination of the samples performed by Biotech Laboratories Pty Ltd Queensland.

Test Area

Air conditioning air ducting system/s. The system is a mixed one. One air handler supplying quite direct air flow to destination terminals. Another had a split air flow system and ducting constructed with large curvature in many places.

Sampling was also performed in a public area access site at the point furthest from the air handler. This site was at a point in a bistro area—in the ceiling close to a window. Sampling was also performed at a public point described as cashier.

Air Supply

The system is refrigerated. The system is idyll for up to 11 hours daily. For part of these trials one air handler was re-set so that the fans worked continuously for 24 hours each day for 7 days. The refrigeration unit was maintained as operational for between 9 and 11 hours. The air is filtered prior to entry into the ducting.

Microbiological Sampling

Sampling for airborne bacterium, airborne fungi and mould, surface bacteria and surface yeast and mould was performed by sterile swab and automatic air sampling apparatus.

Solid Tea Tree Oil Compositions

In order to fully test the efficacy of the solid composition a number of compositions made according to Example 2 were employed.

Sampling Procedure

Samples were taken prior to installing the gel discs. The gel discs were installed either side of the inspection hatch and placed directly on the floor of the air conditioning ducting.

Bacteria

Surface bacteria valued found are insignificant. Airborne values are higher—but may be considered also to be unimportant so far as building health is concerned.

Surface Yeast and Mould and Airborne Fungi and Mould

These are considered high. Species are identified but not described in detail.

Airborne Fungi and Mould

Generally not considered excessive. Results for the public area are indicated for interest.

Temperature and Relative Humidity

Temperatures fluctuated considerably. The relative humidity was high but in line with local atmospheric conditions for the summer period in northern New South Wales.

RESULTS
TEST SITE A—UPPER CASINO

| YEAST AND MOULD CFU/cm2 | | | |
|---|---|---|---|
| | 04/02/97 | 11/02/97 | 18/02/97 |
| ACCESS POINT 1 | | | |
| Hatch Door | 20 | <4 | 4 |
| Hatch Door | <4 | <4 | <4 |
| Ducting Floor | 640 | 320 | 160 |
| Ducting Floor | 960 | 640 | 440 |
| ACCESS POINT 2 | | | |
| CASHIER-PUBLIC PLACE | | | |
| Duct wall - side | 510 | 240 | 330 |
| Duct wall - rear | 180 | 200 | 92 |

On the start date, Feb. 4, 1997, one composition (10% v/v tea tree oil) was installed after sampling. At the test time Feb. 11, 1997 there were only a few grams of the single 10% tea tree oil discs remaining in the ducting.

On the Feb. 18, 1997, two further 10 % v/v tea tree oil compositions were installed. These discs were designed to have slow diffusion rates.

| ACCESS POINT 1 | 25/02/97 | 04/03/97 |
|---|---|---|
| Hatch Door | 4 | 8 |
| Hatch Door | <4 | <4 |
| Ducting Floor | <1200 | 140 |
| Ducting Floor | <1200 | 220 |

At test Feb. 25, 1997 it was found that the solid compositions had diffused slowly and were greater than 80% intact. Following sampling, two further 15% v/v tea tree oil solid compositions were installed. These compositions had a gel type as described in Example 2 and allowed for greater diffusion rate to compensate for the limited air flow in the system.

The results on Mar. 4, 1997 confirm positively this course of action with a reduction in CFUs from <1200 to 140 and 220.

The trials generally indicated a highly contaminated ducting environment and continued as follows.

| ACCESS POINT 1 | 11/03/97 | 18/03/97 | 25/03/97 |
|---|---|---|---|
| Hatch Door | <4 | 4 | <4 |
| Hatch Door | <4 | <4 | <4 |
| Ducting Floor | 380 | 120 | 220 |
| Ducting Floor | 570 | 1200 | 84 |

After Mar. 11, 1997 no further solid compositions were installed. The air flow was very poor during week of Mar. 18, 1997. At Mar. 25, 1997 the compositions had diffused by about 95%.

These tests confirm that the air conditioning fan system is preferably running fully for each 24 hour period to fully maximise the solid composition potential. The refrigeration may be employed only for the commercial times required by the operator—in this instance 9–13 hours daily. Running the fans is a low energy cost. The general benefits of moving large air mass around public facilities irrespective of tea tree oil gel solid composition disinfection are considerable.

Species of micro-organisms were identified during these trials. No conclusive evidence was obtained to indicate the tea tree oil disinfection process is more specific for the elimination of any particular type.

The most dominant species present was *Cladosporium herbarium*, with Penicillium species the next most dominant. Aspergillus and Candida were also observed. It was noted that the Aspergillus only appeared after human intervention with the installation of a new inspection hatch at one ducting site.

TEST SITE B—TERRACE BISTRO
ACCESS POINT 4

Adjacent to a Window in the public bistro area. This area is some 70 metres from the insertion point of the Tea Tree Oil Solid Compositions in the ducting. For four weeks in the trial sampling was conducted as shown below:

| | CFU/cm | | | |
|---|---|---|---|---|
| | 04/02/97 | 11/02/97 | 18/02/97 | 25/02/97 |
| Duct Wall-Side | >1200 | >1200 | >1200 | >1200 |
| Duct Wall-Rear | >1200 | >1200 | >1200 | >1200 |

On the Mar. 4, 1997, one solid composition of the present invention was installed. The count was more fully enumerated following this installation.

| | 04/03/97 | 11/03/97 | 18/03/97 | 25/03/97 |
|---|---|---|---|---|
| Duct Wall-Side | 12000 | 2700 | 18400** | 2600 |
| Duct Wall-Rear | 6800 | 2100 | 1900 | 1400 |

**This anomalous result may be due in part to the reduction in air flow that week. No further compositions were placed in this area after 04/03/97. It is noted that the extremely high counts at this point were effectively reduced over 4 weeks by the insertion only of one 2.2 kilogram tea tree oil solid composition. The significant reduction within one week of these trails - 04/03/97 to 11/03/97 indicate that in an area of high infection such as this, solid compositions can be applied at more regular intervals, or in greater mass per composition.

Test Conclusions

Air flow is preferably continuous. Fans can be left running at low cost. Refrigeration can be employed as required. High relative humidity values are conducive to formation of surface yeast and moulds constant air flow reduces this risk. Tea tree gel discs are preferably moderate release type. Optimum tea tree level found to be 15% v/v. Split air flow ducting—generally considered outdated—must be clearly identified and cycles shown so that tea tree oil disc insertion points can be clearly determined. Tea tree oil gel disc are clearly effective in the elimination of fungus, moulds and yeasts and the maintenance of low bacteria counts in commercial air conditioning ducting.

These examples demonstrate that the Tea Tree Oil Solid Composition of the present invention is highly effective and safe air conditioning ducting system sanitiser. The composition is particularly effective against high mould, fungus and yeast microorganism numbers. The presence of such high levels of micro-organisms is now recognised as posing a serious health risk to the buildings occupants.

The composition is particularly effective in well controlled refrigerated air conditioning systems which run continuously. The constant air flow in such systems allows for even diffusion rates of the solid composition tea tree oil gel discs.

The composition was found to be effective in commercial systems which operated fully for only limited times during any 24 hour period. The trials demonstrated a low cost way for such facilities to further improve the general air quality of their systems. By limiting the generation of refrigerated air to the times selected and at other times running the fans only, the solid composition worked more effectively and the overall air quality improved.

In badly infected systems, the solid composition can return the system to normal and accepted base line values for resident fungal microorganisms. By thereafter employing regular placement of the solid composition in air conditioning facilities these levels are economically and efficiently maintained.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A solid composition including a gum material and tea tree oil wherein the solid composition releases vapour containing the tea tree oil when exposed to an effective flow of gas.

2. A solid composition according to claim 1 wherein the gum material is a carrageenan.

3. A solid composition according to claim 2 wherein the carrageenan includes a kappa, iota or lambda fraction or a mixture of one or more of the fractions.

4. A solid composition according to claim 1 wherein the gum material includes a galactomannan.

5. A solid composition according to claim 4 wherein the galactomannan has a molecular weight of approximately 300,000.

6. A solid composition according to claim 4 wherein the galactomannan is derived from the legume *Ceratonia siliqua*.

7. A solid composition according to claim 4 wherein the galactomannan is locust bean gum.

8. A solid composition according to claim 1 wherein the gum material includes a microbial exudate.

9. A solid composition according to claim 8 wherein the microbial exudate is Xanthan gum.

10. A solid composition according to claim 1 wherein the gum material includes a mixture of two or more components selected from the group consisting of a carageenan, locust bean gum and Xanthan gum.

11. A solid composition according to claim 1 wherein the gum material is present in the solid composition at a concentration of between 2 and 10 wt %.

12. A solid composition according to claim 11 wherein the gum material is present in the solid composition at a concentration of between 3 and 6 wt %.

13. A solid composition according to claim 1 which further includes an aromatic oil.

14. A solid composition according to claim 13 wherein the aromatic oil is selected from at least one of the group consisting of heliotropin, lavender, camomile, a lemon scented oil, the oil of *Leptospermum liversidgeii*, sandalwood and jasmine.

15. A solid composition according to claim 14 wherein the aromatic oil is sandalwood.

16. A solid composition according to claim 13 which further includes a fixative.

17. A solid composition according to claim 16 wherein the fixative is selected from the group consisting of musk ketone, coumerin, eugenol and vanillin.

18. A solid composition according to claim 17 wherein the fixative is eugenol.

19. A solid composition according to claim 1 wherein the natural oil is solubilised by admixture with a non-ionic surfactant.

20. A solid composition according to claim 19 wherein the surfactant is an alcohol ethoxylate.

21. A solid composition according to claim 20 wherein the alcohol ethoxylate is polyoxtethylene(2)oleyl ether.

22. A solid composition according to claim 1 wherein the solid composition is in the shape of a flat discus with a base surface and a top surface and a side wall connecting the base surface to the top surface.

23. A solid composition according to claim 22 wherein the diameter of the top surface is less than the diameter of the base surface.

24. A solid composition according to claim 22 wherein the ratio of the height of the side wall to the width of the top surface is between 1:10 and 1:11.5.

25. A solid composition according to claim 22 wherein the side wall is shaped in a camber.

26. A solid composition according to claim 22 wherein the angle of connection between the base and top surfaces is equal to or less than 65 degrees.

27. A solid composition according to claim 1 wherein the solid composition has a total weight of between 0.5 and 5 kg.

28. A solid composition according to claim 27 wherein the solid composition has a total weight of between 0.9 and 3 kg.

29. A method of preparing a solid composition according to claim 1 which method includes:

i) dissolving a gum material in an aqueous solution;

ii) heating the gum material solution to a temperature of between 60° C. and 95° C.;

iii) admixing the heated gum material solution with tea tree oil solution; and iv) placing the admixed solution from step iii) into a mould.

30. A method according to claim 29 wherein the tea tree oil solution is in admixture with a non-ionic surfactant.

31. A method according to claim 30 wherein the non-ionic surfactant is an alcohol ethoxylate.

32. A method according to claim 31 wherein the alcohol ethoxylate is polyoxyethylene (2) oleyl ether.

33. A method of diffusing tea tree oil into the atmosphere which method includes exposing a solid composition including a gum material and tea tree oil to an air flow such that the solid composition releases vapour containing the tea tree oil.

34. A method according to claim 33 wherein the solid composition further includes an aromatic oil.

35. A method according to claim 33 wherein the solid composition is exposed to an air flow by placing the solid composition in an air conditioning duct.

36. A method of disinfecting an air conditioning system which method includes placing a solid composition in a duct of the air conditioning system, the solid composition including a gum material and tea tree oil, wherein the composition releases antimicrobial vapour containing the tea tree oil when exposed to an effective flow of gas.

37. A method according to claim 36 wherein the solid composition further includes an aromatic oil.

* * * * *